(12) United States Patent
Ikehira et al.

(10) Patent No.: US 6,476,278 B1
(45) Date of Patent: Nov. 5, 2002

(54) PROCESSES FOR THE PREPARATION OF ALCOHOLS

(75) Inventors: Hideyuki Ikehira, Osaka (JP); Kunihiko Murata, Saitama (JP); Eiji Katayama, Kanagawa (JP); Masami Kozawa, Chiba (JP); Toru Yokozawa, Kanagawa (JP); Takeshi Ohkuma, Aichi (JP); Takao Ikariya, Tokyo (JP); Ryoji Noyori, Aichi (JP)

(73) Assignees: Japan Science and Technology Corporation, Saitama (JP); Takasago International Corporation, Tokyo (JP)

( * ) Notice: Subject to any disclaimer, the term of this patent is extended or adjusted under 35 U.S.C. 154(b) by 0 days.

(21) Appl. No.: 09/868,169

(22) PCT Filed: Dec. 15, 1999

(86) PCT No.: PCT/JP99/07035

§ 371 (c)(1), (2), (4) Date: Oct. 25, 2001

(87) PCT Pub. No.: WO00/35845

PCT Pub. Date: Jun. 22, 2000

(30) Foreign Application Priority Data

Dec. 16, 1998 (JP) .......................................... 10-358034

(51) Int. Cl.[7] .............................................. C07C 27/00
(52) U.S. Cl. ...................... 568/814; 568/832; 568/834; 568/835; 568/881
(58) Field of Search ................................. 568/814, 832, 568/881, 834, 835

(56) References Cited

U.S. PATENT DOCUMENTS 5,763,688 A    6/1998    Ikariya et al.

FOREIGN PATENT DOCUMENTS

| JP | 62-129270 | 6/1987 |
| JP | 3-56428 | 3/1991 |
| JP | 10-273455 | 10/1998 |

OTHER PUBLICATIONS

Mestroni, J. Organometallic Chemistry, vol. 140, pp. 63–72 (1977).*

Botteghi, J. Organometallic Chemistry, vol. 304, pp. 217–225 (1986).*

Frediani, J. Organometallic Chemistry, vol. 498, pp. 187–197 (1995).*

M.A. Bennett et al., Comprehensive Organometallic Chemistry, vol. 4, pp. 931–965 (1982).

V. Penicaud, et al., Eur. J. Org. Chem., vol. 7, pp. 1745–1748 (1999).

Michael A. Weiner, et al., Inorg. Chem., vol. 19, No. 9, pp. 2797–2800 (1980).

* cited by examiner

*Primary Examiner*—Michael L. Shippen
(74) *Attorney, Agent, or Firm*—Wenderoth, Lind & Ponack, L.L.P.

(57) ABSTRACT

Alcohols are produced in a practical and advantageous method, by the hydrogenation of a carbonyl compound under mild conditions, by reacting the carbonyl compounds with hydrogen in the presence of a bipyridyl derivative, a group VIII transition metal complex, and a base, or by reducing a carbonyl compound in the presence of a bipyridyl derivative, a group VIII transition metal complex, a base, and an alcoholic solvent.

4 Claims, No Drawings

PROCESSES FOR THE PREPARATION OF ALCOHOLS

TECHNICAL FIELD

The invention of this application relates to a method for producing alcohols.

More specifically, the invention of this application relates to an advantageous method for producing alcohols useful as synthetic intermediates of medical drugs or agricultural chemicals or as synthetic intermediates of various general-purpose chemical products using carbonyl compounds as a raw material

BACKGROUND ART

As a method in which carbonyl compounds are hydrogenated using a homogeneous catalyst to produce the corresponding alcohols, such methods as described in Eds. G. Wilkinson, F. G. A. Stone and E. W. Abel, Comprehensive Organometallic Chemistry, Vol. 4, p 931 (1982), using a ruthenium complex, are known.

However, since the hydrogenation activity was low for the above-described method, and a relatively high temperature or high hydrogen pressure was required, it was not necessarily suitable for practical use.

OBJECTIVE OF THE INVENTION

Accordingly, the invention of this application aims to solve the aforesaid problems of the prior technique, and to provide a practical advantageous novel method for producing alcohols, by which the alcohols may be produced efficiently by the hydrogenation of carbonyl compounds under milder conditions, without requiring condition such as high temperature or high hydrogen pressure, as in conventional methods.

As a solution of the above-mentioned problems, the invention of the present application firstly provides a method for producing alcohols, comprising reacting carbonyl compounds with hydrogen in the presence of a bipyridyl derivative, a group VIII transition metal complex and a base.

Further, the invention of the present application secondly provides a method for producing alcohols, comprising the reduction of carbonyl compounds in the presence of a bipyridyl derivative, a group VIII transition metal complex, a base and an alcoholic solvent. Further, the invention of the present application thirdly provides the above method, wherein the base is a hydroxide or a salt of an alkali metal or an alkaline earth metal, or a quaternary ammonium salt. Fourthly, the present invention provides the above method, wherein the carbonyl compounds are represented by the following general formula (a):

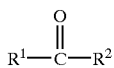
(a)

(wherein $R^1$ and $R^2$ may be the same or different, each representing a hydrogen atom, a halogen atom, an alkyl group which may contain a substituent, an aralkyl group which may contain a substituent, an aryl group which may contain a substituent, an alkenyl group which may contain a substituent, an alkoxyl group which may contain a substituent or an alkyloxycarbonyl group, or $R^1$ and $R^2$ may be bound to form a cyclic compound, and $R^1$ and $R^2$ may not both be hydrogen atoms at the same time). Fifthly, the present invention provides any of the first to fourth methods, wherein the group VIII transition metal complex is represented by the following general formula (b):

(b)

(wherein $M^1$ represents rhodium, ruthenium, iridium or platinum, x represents a hydrogen atom, a halogen atom, a carboxyl group, an alkoxy group or a hydroxy group, L represents an organic ligand, and m and n are each an integer of 0 to 6 where $0 < m+n \leq 6$) Sixthly, the present invention provides any of first to fourth methods, wherein the bipyridyl derivative is represented by the following general formula (c):

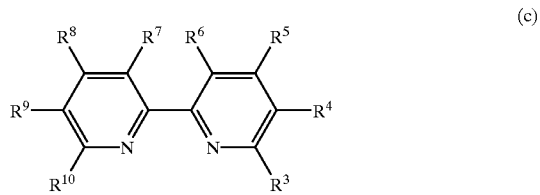
(c)

(wherein $R^3$, $R^4$, $R^5$, $R^6$, $R^7$, $R^8$, $R^9$ and $R^{10}$ may be the same or different, and represent a hydrogen atom, a halogen atom, an alkyl group which may contain a substituent, an aralkyl group which may contain a substituent, an aryl group which may contain a substituent or an alkenyl group which may contain a substituent).

BEST MODE FOR CARRYING OUT THE INVENTION

The invention of the present application has the above-mentioned characteristics, and the embodiments thereof are described below.

First, in the invention of the present application, carbonyl compounds are used as a raw material, and may be chosen from various compounds, such as those represented by the above-mentioned general formula (a).

The substituents $R^1$ and $R^2$ of the carbonyl compound represented by the general formula (a), may be halogen atoms such as fluorine atom, chlorine atom, bromine atom, iodine atom and the like, alkyl groups such as methyl group, ethyl group, n-propyl group, isopropyl group, n-butyl group, isobutyl group, t-butyl group, n-amyl group, neopentyl group, n-hexyl group, cyclohexyl group, n-octyl group, n-nonyl group, menthyl group, 2,3,4,-trimethyl-3-pentyl group, 2,4-dimethyl-3-pentyl group and the like, aralkyl groups such as benzyl group, 2-phenylethyl group, 2-naphthylethyl group, diphenylmethyl group and the like, aryl groups such as phenyl group, naphthyl group, biphenyl group, furyl group, thiophenyl group and the like, alkenyl groups such as 2-methyl-1-propenyl group, 2-butenyl group, trans-β-styryl group, 3-phenyl-1-propenyl group, 1-cyclohexenyl group and the like, alkoxyl groups such as methoxy group, ethoxy group, n-propoxy group, t-butoxy group and the like, aryloxy groups such as phenoxy group and the like, and alkyloxycarbonyl groups such as methoxycarbonyl group, ethoxycarbonyl group, t-butyloxycarbonyl group, benzyloxycarbonyl group, phenyloxycarbonyl group and the like. When these groups are further substituted with substituents, examples of such substituents include the above-mentioned halogen atoms, the above-mentioned alkoxyl groups, the above-mentioned aryloxy groups, lower alkyl groups such as methyl group, ethyl group, isopropyl group, n-butyl group, t-butyl group, n-amyl group, n-hexyl group and the like, lower alkylthio groups such as n-propylthio group, t-butylthio group and the like, arylthio groups such as phenylthio group and the like, nitro group, hydroxyl group and the like.

Typical examples of the specific carbonyl compounds are acetone, acetophenone, benzaldehyde, benzalacetone, cyclohexane, benzophenone, substitution compounds thereof and the like.

Further, as the group VIII transition metal complex. compounds such as those represented by the general formula (b) may be mentioned as examples.

The organic ligand: L, includes CO, NO, $NH_2$, $NH_3$ and the like, as well as olefin ligands, acetylene ligands, aromatic compound ligands, organic oxygen-containing compound ligands, organic sulfur-containing compound ligands, organic nitrogen-containing compound ligands and the like.

Examples of the olefin ligand include ethylene, propylene, butadiene, cyclohexene, 1,3-cyclohexadiene, 1,5-cyclooctadiene, cyclooctatriene, norbornadiene, acrylic acid ester, methacrylic acid ester, cyclopentadienyl, pentamethylcyclopentadienyl and the like. Further, 5-membered compounds represented by the following general formula exemplify the 5-membered compounds which are generally used as ligands

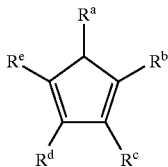

(wherein $R^a$ to $R^e$ may be the same or different substituents, and represent a hydrogen atom, a halogen atom, an alkyl group which may contain a substituent, an aralkyl group which may contain a substituent, an aryl group which may contain a substituent, an alkenyl group which may contain a substituent, an alkoxyl group which may contain a substituent or an alkyloxycarbonyl group.

Specifically, examples of the halogen atom, the halogen atoms include fluorine atom, chlorine atom, bromine atom, iodine atom and the like, examples of the alkyl group include methyl group, ethyl group, n-propyl group, isopropyl group, n-butyl group, isobutyl group, t-butyl group, n-amyl group, neopentyl group, n-hexyl group, cyclohexyl group, n-octyl group, n-nonyl group, menthyl group, 2,3,4-trimethyl-3-pentyl group, 2,4-dimethyl-3-pentyl group and the like, examples of the aralkyl group include benzyl group, 2-phenylethyl group, 2-naphthylethyl group, diphenylmethyl group and the likes examples of the aryl group include phenyl group, naphthyl group, biphenyl group, furyl group, thiophenyl group and the like, examples of the alkenyl group include 2-methyl-1-propenyl group, 2-butenyl group, trans-β-styryl group, 3-phenyl-1-propenyl group, 1-cyclohexenyl group and the like, examples of the alkoxyl group include methoxy group, ethoxy group, n-propoxy group, t-butoxy group and the like, examples of the aryloxy group include phenoxy group and the like, and examples of the alkyloxycarbonyl group include methoxycarbonyl group, ethoxycarbonyl group, t-butyloxycarbonyl group, benzyloxycarbonyl group, phenyloxycarbonyl group and the like. when these groups are further substituted with substituents, examples of the substituents include the above-mentioned halogen atoms, the above-mentioned alkoxyl groups, the above-mentioned aryloxy groups, lower alkyl groups such as methyl group, ethyl group, isopropyl group, n-butyl group, t-butyl group, n-amyl group, n-hexyl group and the like, lower alkylthio groups such as n-propylthio group, t-butylthio group and the like, arylthio groups such as phenylthio group and the like, nitro group, hydroxyl group and the like.

Examples of acetylene ligands as the organic ligand:L include acetylene, 1,2-dimethylacetylene, 1,4-pentadiyne, 1,2-diphenylacetylene and the like.

Examples of aromatic compound ligands include benzene, p-cymene, mesitylene, hexamethylbenzene, naphthalene, anthracene and the like. However, examples of aromatic compound often used in general as ligands, are cyclic aromatic compounds represented by the following general formula:

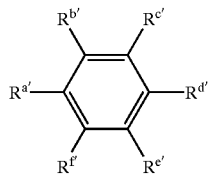

(wherein $R^{a'}$ to $R^{f'}$ may be the same or different, representing a hydrogen atom, a saturated or unsaturated hydrocarbon group, an aryl group or a heteroatom-containing functional group; for example, alkyl groups such as methyl, ethyl, propyl, isopropyl, butyl, t-butyl, pentyl, hexyl, heptyl and the like, cycloalkyl groups such as cyclopropyl, cyclobutyl, cyclopentyl, cyclohexyl and the like, unsaturated hydrocarbon groups such as benzyl, vinyl, allyl, phenyl, naphthyl and the like, and heteroatom-containing functional groups such as hydroxyl group, alkoxy group, alkoxycarbonyl group and the like.

Further, examples of organic oxygen-containing compound ligands as the organic ligand: L include acetate, benzoate, acetylacetonate and the like. Examples of organic sulfur-containing compound ligands include dimethyl sulfoxide. dimethyl sulfide, thiophene, carbon disulfide, carbon sulfide, thiophenol and the like. Examples of the organic nitrogen-containing compound ligand include acetonitrile, benzonitrile, t-butylisocyanide, pyridine, 1,10-phenanthroline, 2,2'-bipyridyl and the like.

Specific examples of the group VIII transition metal complex of the present invention include chloro tris (triphenylphosphine)rhodium (I), cyclopentadienyl bis (triphenylphosphine)rhodium (I), bis(cyclooctadiene) diiododirhodium (I), chloro(cyclopentadienyl) bis (triphenylphosphine)ruthenium (II), chloro (pentarethylcyclopentadienyl) (1,3-bis(diphenylphosphino) propane)ruthenium (II), chloro (pentamethylcyclopentadienyl) (1,5-cyclooctadiene) ruthenium (II), dichlorotris(triphenylphosphine)ruthenium (II), chlorotris(triphenylphosphine)iridium (I), pentamethylcyclopentadienylbis(ethylene)iridium (I) (ethylene)bis(triphenylphosphine)platinum (0), trans-[chloro(ethyl)bis(triethylphosphine)platinum (II)], cis-[diethylbis(triethylphosphine)platinum (II)], dichloro (norbornadiene)platinum (II) tetrakis(triphenylphosphine) platinum (0) and the like. Among such compounds, ruthenium complexes exhibit an especially high activity of course, the complex used in the present invention is not limited to those mentioned above.

Although the amount of the group VIII transition metal complex used varies depending on the reaction vessel or the economics, it may be used with a molar ratio of 1/100 to 1/100,000, preferably 1/200 to 1/10,000 to the reaction substrate, the carbonyl compound.

Furthermore, the base used in the present invention is represented, for example, by the general formula $$M^2Y$$

wherein $M^2$ is an alkali metal or an alkaline earth metal, and Y is a hydroxyl group, an alkoxy group, a mercapto group or a naphthyloxy group. Specific examples thereof include KOH, $KOCH_3$, $KOCH(CH_3)_2$, $KC_{10}H_6$, LiOH, $LiOCH_3$, $LiOCH(CH_3)_2$ and the like. Further, a quaternary ammonium salt may likewise be used as the base.

The amount of the base used is preferably 0.5 to 100 equivalents, more preferably 2 to 40 equivalents to the group VIII transition metal complex.

As the bipyridyl derivative used in the present invention, the bipyridyl derivative represented by the above-mentioned general formula (c) may be used.

Specifically, in the substituents $R^3$, $R^4$, $R^5$, $R^6$, $R^7$, $R^8$, $R^9$ and $R^{10}$, examples of the halogen atom include fluorine atom, chlorine atom, bromine atom, iodine atom and the like, examples of the alkyl group include methyl group, ethyl group, n-propyl group, isopropyl group, n-butyl group, isobutyl group, t-butyl group, n-amyl group, neopentyl group, n-hexyl group, cyclohexyl group, n-octyl group, n-nonyl group, menthyl group, 2,3,4-trimethyl-3-pentyl group, 2,4-dimethyl-3-pentyl group and the like, examples of the aralkyl group include benzyl group, 2-phenylethyl group, 2-naphthylethyl group, diphenylmethyl group and the like, examples of the aryl group include phenyl group, naphthyl group, biphenyl group, furyl group, thiophenyl group and the like, and examples of the alkenyl group include 2-methyl-1-propenyl group, 2-butenyl group, trans-β-styryl group, 3-phenyl-1-propenyl group, 1-cyclohexenyl group and the like. Examples of the specific bipyridyl compounds include 2,2'-bipyridyl, 4,4'-diphenyl-2,2'-bipyridyl, 4,4'dimethyl-2,2'-bipyridyl, 3,3'-diphenyl-2,2'-bipyridyl, 3,3'-diethyl-2,2'-bipyridyl etc.

The amounts of these bipyridyl derivatives are in the range of 0.5 to 20 equivalents, preferably 1 to 6 equivalents to the transition metal complex.

In the method for producing alcohols of the invention, the addition of these bipyridyl derivatives is indispensable, and as described in the comparative example, the absence of such derivatives lead to a drastic decrease in the yield of the reduction product.

Further, in the present invention, a solvent is usually employed. As the solvent, a solvent that solubilizes the reaction raw material and the catalyst system is preferably used. As specific examples, aromatic solvents such as toluene, xylene and the like, aliphatic solvents such as pentane, hexane and the like, halogen-containing hydrocarbon solvents such as methylene chloride and the like, ether-type solvents such as ether, tetrahydrofuran and the like, alcoholic solvents such as methanol, ethanol, 2-propanol, butanol, benzyl alcohol and the like, and heteroatom-containing organic solvents such as acetonitrile, DMF, N-methylpyrrolidone, pyridine and DMSO may be applicable. Since the products are alcohols, the use of alcoholic solvents are preferable. These solvents may be used either singly or as a mixed solvent.

The amount of the solvent used may be determined, as required, depending on the solubility of the reaction substrate and the economics. For example, in case of 2-propanol, the reaction may be conducted at a low substrate concentration of 1% or less, or at an approximately solvent-free state with only the substrate. However, it may preferably be used in the range of 20 to 50 wt %.

The pressure of hydrogen in the invention is usually in the range of 1 to 200 atm, preferably in the range of 3 to 100 atm. However, when an alcoholic solvent such as 2-propanol or the like is used, a hydrogen transfer-type reaction proceeds without the addition of hydrogen gas.

The reaction temperature may usually be within the range of −40 to 120° C. However, with consideration to the economies, it is preferable to conduct the reaction at a temperature of 15° C. to 100° C.; the reaction, therefore, may be conducted at a temperature of 25 to 40° C., close to room temperature. Incidentally, the present invention is also characteristic in that the reaction proceeds even at a low temperature of −30 to 0° C.

The reaction time varies depending on the reaction conditions such as the concentration of the reaction substrate, the temperature, and the pressure. Usually, the reaction is completed within a few minutes to 30 hours.

The reaction may be conducted in batch or continuous reaction system.

EXAMPLES

The invention is illustrated more specifically by referring to the following Examples. However, the present invention is not limited to these Examples.

Example 1

RuClCp* (cod) namely, chloro (pentamethylcyclopentadienyl) (1,5-cyclooctadiene)-ruthenium (II) (3.8 mg, 0.01 mmol), KOH (0.04 mmol), 2,2'-bipyridyl (3.1 mg, 0.02 mmol), and acetophenone (600.75 mg. 5.0 mmol) were dissolved in 10 ml of 2-propanol, deaerated by argon substitution, after which the total amount of the resulting mixture was transferred into a 100-milliliter metallic autoclave. Hydrogen was then charged to a predetermined pressure (50 atm), and the reaction was started at room temperature (28° C.). After the reaction solution was stirred for 3 hours, the reaction pressure was brought back to atmospheric pressure, and the reaction product, 1-phenyl ethanol, was identified and determined by TLC monitor (silica gel: n-hexane/ethyl acetate= 4/1), high performance liquid chromatography and NMR of the reaction solution. The reaction substrate was completely consumed, and the yield of the product was 99% or more.

Example 2

RuClCp* (cod) (3.8 mg, 0.01 mmol), KOH (0.04 mmol), 2,2'-bipyridyl (3.1 mg, 0.02 mmol) and benzalacetone (730.95 mg, 5.0 mmol) were dissolved into 10 ml of 2-propanol, and deaerated by argon substitution, after which the total amount of the resulting mixture was transferred into a 100-milliliter metallic autoclave. Hydrogen was then charged to a predetermined pressure (50 atm), and the reaction was started at room temperature (28° C.). After the reaction solution was stirred for 3 hours, the reaction pressure was brought back to atmospheric pressure, and the reaction products, 4-phenyl-2-butanone (yield 19.8%) and 4-phenyl-2-butanol (yield 80.2%), were identified and determined by TLC monitor (silica gel: n-hexane/ethyl acetate= 4/1) and gas chromatography of the reaction solution.

Example 3

RuClCp* (cod) (3.8 mg, 0.01 mmol), KOH (0.04 mmol), 2,2'-bipyridyl (3.1 mg, 0.02 mmol) and benzalacetone (730.95 mg, 5.0 mmol) were dissolved into 10 ml of 2-propanol, and deaerated by argon substitution, after which the total amount of the resulting mixture was transferred into a 100-milliliter metallic autoclave. Hydrogen was then charged to a predetermined pressure (4 atm), and the reaction was started at room temperature (28° C.) After the reaction solution was stirred for 18 hours, the reaction pressure was brought back to atmospheric pressure, and the reaction product, 4-phenyl-2-butanone (yield 87.7%), was identified and quantitatively determined by TLC monitor (silica gel: n-hexane/ethyl acetate=4/1) and gas chromatography of the reaction solution. At this time, 12.3% of the raw material, benzalacetone, was recovered.

Example 4

RuClCp* (cod) (3.8 mg, 0.01 mmol), KOH (0.04 mmol), 2,2'-bipyridyl (3.1 mg, 0.02 mmol) and 4-t-butylcyclohexanone (385.63 mg. 2.5 mmol) were dissolved into 10 ml of 2-propanol. and deaerated by argon substitution, after which the total amount of the resulting mixture was transferred into a 100-milliliter metallic autoclave. Hydrogen was then charged to a predetermined pressure (4 atm), and the reaction was started at room temperature (28° C.) After the reaction solution was stirred for 18 hours, the reaction pressure was brought back to atmospheric pressure, and the reaction products, cis-4-t-bucylcyclohexanol (yield 23.2 and trans-4-t-butylcyclohexanol (yield 38.2%), were identified and quantitatively determined by TLC monitor (silica gel: n-hexane/ethyl acetate=4/1) and gas chromatography of the reaction solution, Example 5

RuClCp* (cod) (3.8 mg, 0.01 mmol), KOH (0.04 mmol), 2,2'-bipyridyl (3.1 mg, 0.02 mmol) and 4-t-butylcyclohexanone (385.63 mg, 2.5 mmol) were dissolved into 10 ml of 2-propanol, and deaerated by argon substitution, after which the total amount of the resulting mixture was transferred into a 100-milliliter metallic autoclave. Then, the reaction was started at room temperature (28° C.) while conducting argon substitution. After the reaction solution was stirred for 18 hours, the reaction produces, cis-4-t-butylcyclohexanol (yield 8.6%) and trans-4-t-butylcyclohexanol (yield 21.1%), were identified and quantitatively determined by TLC monitor (silica gel: n-hexane/ethyl acetate=4/1) and gas chromatography of the reaction solution. Here, 35.0% of the raw material, 4-t-butylcyclohexanone, was recovered.

Comparative Example 1

RuClCp (cod) (3.8 mg, 0.01 mmol), KOH (0.04 mmol) and acetophenone (600.75 mg, 5.0 mmol) were dissolved into 10 ml of 2-propanol. After deaeration by argon substitution, the total amount of the resulting mixture was transferred into a 100-milliliter metallic autoclave. Hydrogen was then charged to a predetermined pressure (50 atm), and the reaction was started at room temperature (28° C.) After the reaction solution was stirred for 3 hours, the reaction pressure was brought back to atmospheric pressure, and the reaction product, 1-phenyl ethanol, was identified and quantitatively determined by TLC monitor (silica gel: n-hexane/ethyl acetate=4/1), high-performance liquid chromatography and NMR of the reaction solution. 97% of the reaction substrate remained, and the yield of the product was 3% or less.

INDUSTRIAL APPLICABILITY

As has been described in detail above, the invention of the present application enables producing alcohols by hydrogenation of carbonyl compounds, under a much milder condition than that known in the past. Hence, a method for producing alcohols, which is practical and advantageous, is provided.

What is claimed is:

1. A method for producing alcohols, comprising the reaction of carbonyl compounds with hydrogen in the presence of a 2,2'-bipyridyl, a ruthenium complex represented by the following general formula (b)

$$M^1X_mL_n \tag{b}$$

wherein $M^1$ represents ruthenium, X represents a hydrogen atom, a halogen atom, an alkoxy group or a hydroxy group, L represents an organic ligand, and m and n are each an integer of 0 to 6 where $0<m+n\leqq6$, and a base selected from the group consisting of a hydroxide of an alkali metal, a salt of an alkali metal, a hydroxide of an alkaline earth metal, a salt of an alkali earth metal, and a quaternary ammonium salt, at a temperature of 25 to 40° C.

2. A method for producing alcohols, comprising the reduction of carbonyl compounds in the presence of a 2,2'-bipyridyl, a ruthenium complex represented by the following general formula (b)

$$M^1X_mL_n \tag{b},$$

wherein $M^1$ represents ruthenium, X represents a hydrogen atom, a halogen atom, an alkoxy group or a hydroxy group, L represents an organic ligand, and m and n are each an integer of 0 to 6 where $0<m+n<6$, a base selected from the group consisting of a hydroxide of an alkali metal, a salt of an alkali metal, a hydroxide of an alkaline earth metal, a salt of an alkali earth metal and a quaternary ammonium salt, and an alcoholic solvent, at a temperature of 25 to 40° C.

3. The method of claim 1, wherein the carbonyl compound is represented by the following general formula (a)

(a)

wherein $R^1$ and $R^2$ may be the same or different, each representing a hydrogen atom, a halogen atom, an alkyl group which may contain a substituent, an aralkyl group which may contain a substituent, an aryl group which may contain a substituent, an alkenyl group which may contain a substituent, an alkoxyl group which may contain a substituent or an alkyloxycarbonyl group, or $R^1$ and $R^2$ may be bound to form a cyclic compound, and $R^1$ and $R^2$ may not be hydrogen atoms at the same time.

4. The method of claim 2, wherein the carbonyl compound is represented by the following general formula (a)

(a)

wherein $R^1$ and $R^2$ may be the same or different, each representing a hydrogen atom, a halogen atom, an alkyl group which may contain a substituent, an aralkyl group which may contain a substituent, an aryl group which may contain a substituent, an alkenyl group which may contain a substituent, an alkoxyl group which may contain a substituent or an alkyloxycarbonyl group, or $R^1$ and $R^2$ may be bound to form a cyclic compound, and $R^1$ and $R^2$ may not be hydrogen atoms at the same time.

* * * * *